United States Patent [19]

Brown et al.

[11] Patent Number: 5,792,777

[45] Date of Patent: Aug. 11, 1998

[54] BIPHENYL QUINUCLIDINES

[75] Inventors: George Robert Brown, Wilmslow; Peter John Harrison, deceased, late of Macclesfield, by Alison Harrison, heir; Keith Blakeney Mallion, Knutsford, all of England

[73] Assignee: Zeneca Limited, London, United Kingdom

[21] Appl. No.: 81,367

[22] PCT Filed: Oct. 27, 1992

[86] PCT No.: PCT/GB92/01968

§ 371 Date: Jun. 30, 1993

§ 102(e) Date: Jun. 30, 1993

[30] Foreign Application Priority Data

Oct. 30, 1991 [GB] United Kingdom ............... 9122988

[51] Int. Cl.⁶ ..................... A61K 43/40; C07D 453/00
[52] U.S. Cl. .............................. 514/305; 546/133
[58] Field of Search ...................... 546/133; 514/305

[56] References Cited

U.S. PATENT DOCUMENTS

| | | |
|---|---|---|
| 3,405,134 | 10/1968 | Judd . |
| 3,534,053 | 10/1970 | Sallay et al. . |
| 3,586,694 | 6/1971 | Shen et al. . |
| 3,655,675 | 4/1972 | Carabateas . |
| 3,679,690 | 7/1972 | Carabateas . |
| 3,725,410 | 4/1973 | Potoski et al. . |
| 3,763,168 | 10/1973 | Carabateas . |
| 3,857,848 | 12/1974 | Mauvernay et al. . |
| 4,038,402 | 7/1977 | Kaminka et al. . |
| 4,599,344 | 7/1986 | Morgan, Jr. . |
| 5,135,935 | 8/1992 | Alberts et al. . |
| 5,242,914 | 9/1993 | Kawamoto et al. . |
| 5,286,864 | 2/1994 | Walther et al. . |
| 5,385,912 | 1/1995 | Neuenschwander et al. . |
| 5,494,918 | 2/1996 | Neuenschwander et al. ......... 514/305 |
| 5,554,613 | 9/1996 | Mallion ............................... 514/253 |

FOREIGN PATENT DOCUMENTS

| | | |
|---|---|---|
| 77130 | 11/1991 | Australia . |
| 1014958 | 8/1977 | Canada . |
| 0330826 | 2/1988 | European Pat. Off. . |
| 0316718 | 5/1989 | European Pat. Off. . |
| 0322182 | 6/1989 | European Pat. Off. . |
| 0328200 | 8/1989 | European Pat. Off. . |
| 0337637 | 10/1989 | European Pat. Off. . |
| 0370415 | 5/1990 | European Pat. Off. . |
| 0412797 | 2/1991 | European Pat. Off. . |
| 0458214 | 11/1991 | European Pat. Off. . |
| 0 497 415 | 8/1992 | European Pat. Off. . |
| 2 323 303 | 12/1973 | Germany . |
| 25 02 916 | 11/1975 | Germany . |
| 4116582 | 11/1991 | Germany . |
| 1416958 | 12/1975 | United Kingdom . |
| 2169292 | 7/1986 | United Kingdom . |
| 9215579 | 9/1992 | WIPO . |
| 93/16048 | 8/1993 | WIPO . |
| 9315073 | 8/1993 | WIPO . |

OTHER PUBLICATIONS

Turchin et al., Stereochemistry of Quinuclidines Containing a Substituent with Aryl (Heteroaryl) Nuclei at Position Three, Khimiko–farmatsevticheskii Zhurnal, 1986, vol. 20, pp. 65–72.

Bondarenko et al., Khim Farm, 12(11), 1978, pp. 56–60. Khim. Farm., 7(8), 1973, 20–24.

Ricciardi et al., Facile Synthesis of Strylquinuclidines, Heterocycles, 24, (1986), pp. 971–977.

Khim. Geterosikl Soedin, 3 (1983), 381–385.

Mikhlina et al., Synthesis and Properties of (3–Quinuclidyl)Diarylcarbinols, Khim. Geterosikl Soedin, 7, 1976, 776–780.

Sekine et al, Effect of Sulfur Containing Purine Nucleosides on Immunological Reaction in Mice, Japan J. Exp. Med, 1973, vol. 43, 5, pp. 369–375.

DeVito et al, Synthesis and Pharmacological Evaluation of Some Novel 13–[N,N]dialkylamino–alkylbenzo[g][2]benzopyrano[43–b]indol–5[13H]ones, Med. Chem. Res, 1(1), (1991), pp. 47–51.

Ermakov et al, Application of Mass Spectrometry in Structural and Stereochemical Investigaions . . . , Khim. Geterosikl Soedin, 10, (1975), 1376–1383.

Mikhlina et al, Stereochemistry of Benzo[b]quinclindes . . . . Khim. Geterosikl Soedin, 6, (1973), pp. 839–843.

Fleet et al, Complex Quinuclidines (1–Azabicyclo[2.2.2.] octanes) from Sugars: Synthesis of 1α,3α,4α,5α)–Quinuclidine–3,5–diol from D–Glucose, J. Chem. Soc. Perkin. Trans., 1(5), (1989), 1067–1068.

(List continued on next page.)

Primary Examiner—Richard L. Raymond
Attorney, Agent, or Firm—Cushman Darby & Cushman Intellectual Property Group of Pillsbury Madison & Sutro, LLP

[57] ABSTRACT

Biphenylylquinuclidine compounds of the formula I:

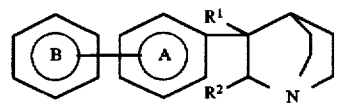

and pharmaceutically-acceptable salts thereof; wherein $R^1$ is hydrogen or hydroxy; $R^2$ is hydrogen; or $R^1$ and $R^2$ are joined together so that $CR^1$-$CR^2$ is a double bond; and one or both ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C) alkylamino, di-[(1–6C)alkyl]amino, N-[(1–6C)alkyl] carbamoyl, N,N-di-[(1–6C)alkyl]carbamoyl, (1–6C) alkoxycarbonyl, (1–6C)alkylthio, (1–6C)alkylsulphinyl, (1–6C)alkylsulphonyl and halogeno-(1–6C)alkyl; are inhibitors of squalene synthase and are hence useful in treating diseases or medical conditions such as hypercholesterolemia, atherosclerosis and fungal diseases. Methods of using these compounds to treat such conditions, novel compounds, processes for making these compounds and pharmaceutical compositions containing them are claimed.

17 Claims, No Drawings

OTHER PUBLICATIONS

E.J. Warawa et al., Quinuclidine Chemistry.2.Syntehsis and Antiinflammatory Properties of 2-Sustituted Benzhydryl-3-quinuclidinols, Journal of Medicinal Chemistry, 1974, vol. 17, No. 5, pp. 497–501.

John Saunders et al., Novel Quinuclidine-Based Ligands for the Muscarinic Cholinergic Receptor, Journal of Medicinal Chemistry, 1990, vol. 33, No. 4, pp. 1128–1137.

Abstract, 89-242612/34: Feb. 3, 1988-DE-803135 (+DE-901735) (Aug. 17, 1989).

Sterling, "Quaternary and tertiary ...", J. Pharm. Sci., vol. 80 No 8 Aug. 1991 pp. 785–789.

BIPHENYL QUINUCLIDINES

The present application is a 371 of PCT/GB92/01968, filed Oct. 27, 1992.

FIELD OF INVENTION

This invention concerns heterocyclic compounds which are useful in inhibiting squalene synthetase, processes for their preparation and pharmaceutical compositions containing them. The present invention is also concerned with methods of using such heterocyclic compounds in diseases and medical conditions where inhibition of squalene synthetase is desirable, for example in treating diseases or medical conditions such as hypercholesterolemia and atherosclerosis.

BACKGROUND

Several different classes of compounds have been reported to possess the capability of being able to lower cholesterol levels in blood plasma. For example agents which inhibit the enzyme HMG CoA reductase, which is essential for the production of cholesterol, have been reported to reduce levels of serum cholesterol. Illustrative of this class of compounds is the HMG CoA reductase inhibitor known as lovastatin which is disclosed in U.S. Pat. No 4,231,938. Other agents which are reported to lower serum cholesterol include those which act by complexing with bile acids in the intestinal system and which are hence termed "bile acid sequestrants". It is believed that such agents act by sequestering bile acids within the intestinal tract. This results in a lowering of the levels of bile acid circulating in the enteroheptatic system and promoting replacement of bile acids by synthesis in the liver from cholesterol, which synthesis results, inter alia, in a lowering of circulating blood cholesterol levels.

Squalene synthetase (also referred to as squalene synthase in the art) is a microsomal enzyme which catalyses the first committed step of cholesterol biosynthesis. Two molecules of farnesyl pyrophosphate (FPP) are condensed in the presence of the reduced form of nicotinamide adenine dinucleotide phosphate (NADPH) to form squalene. The inhibition of this committed step to cholesterol should leave unhindered biosynthetic pathways to ubiquinone, dolichol and isopentenyl t-RNA. Elevated cholesterol levels are known to be one of the main risk factors for ischaemic cardiovacsular disease. Thus, an agent which inhibits squalene synthetase should be useful in treating diseases and medical conditions in which a reduction in the levels of cholesterol is desirable, for example hypercholesterolemia and atherosclerosis.

Thus far, the design of squalene synthetase inhibitors has concentrated on the preparation of analogues of the substrate farnesyl pyrophosphate (FPP), and hence on compounds which contain phosphorus groups. For example, the preparation of phosphorous-containing squalene synthetase inhibitors is reported in published European Patent Application No. 409,181; and the preparation of isoprenoid (phosphinylmethyl)phosphonates as inhibitors of squalene synthetase is reported by Biller et al. J. Med. Chem., 1988, 31, 1869.

Certain quinuclidine derivatives have been reported in EP 412,797 to stimulate central muscarinic acetylcholine receptors. Qunicluidine derivatives which inhibit choline uptake are reported by G H Sterling et al. in J Pharm Sci, (1991), 80(8), 785–789.

SUMMARY OF INVENTION

The present invention is based on the discovery that certain heterocyclic compounds are inhibitors of squalene synthetase, and are hence useful in treating diseases and medical conditions in which inhibition of squalene synthetase is desirable.

According to the present invention there is provided the use of a biphenylylquinuclidine compound of formula I (formula set out hereinafter together with the other chemical formulae referred to herein), or a pharmaceutically-acceptable salt thereof, wherein: $R^1$ is hydrogen or hydroxy; $R^2$ is hydrogen; or $R^1$ and $R^2$ are joined together so that $CR^1$–$CR^2$ is a double bond; and one or both ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl; for the manufacture of a medicament for treating diseases or medical conditions in which inhibition of squalene synthetase is desirable.

The compounds of the present invention are squalene synthetase inhibitors and hence possess the property of inhibiting cholesterol biosynthesis. Thus the compounds of the present invention will be useful in treating diseases or medical conditions in which an inhibition of squalene synthetase is desirable, for example those in which a lowering of the level of cholesterol is blood plasma is desirable. In particular, the compounds of the present invention will be useful in treating hypercholesterolemia and/or ischaemic diseases associated with atheromatous vascular degeneration such as atherosclerosis. The compounds of the present invention will also be useful in treating fungal infections.

Thus according to a further feature of the present invention there is provided a method of inhibiting squalene synthetase in a warm-blooded animals (such as man) requiring such treatment, which method comprises administering to said animal an effective amount of a compound of formula I (as herein defined), or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I (as herein defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

It will be understood that when formula I compounds contain a chiral centre, the compounds of the invention may exist in, and be isolated in, optically active or racemic form. The invention includes any optically active or racemic form of a compound of formula I which possesses the beneficial pharmacological effect of inhibiting squalene synthetase. The synthesis of optically active forms may be carried out by standard techniques of organic chemistry well known in the art, for example by, resolution of a racemic form, by synthesis from optically active starting materials or by asymmetric synthesis.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

It will be appreciated that when $R^1$ and $R^2$ are joined so that $CR^1$–$CR^2$ is a double bond, the heterocyclic ring in formula I will comprise the 2,3-dehydroquinuclidine moiety shown in formula Ia.

A particular value for an alkyl substituent which may be present on ring A or ring B is, for example, (1–4C)alkyl, such as methyl, ethyl, propyl, isopropyl, butyl, isobutyl or sec-butyl.

A particular value for alkoxy substituent which may be present on ring A or ring B is, for example, (1–4C)alkoxy, such as methoxy, ethoxy, propoxy, isopropoxy or butoxy.

A particular value for an alkylamino substituent which may be present on ring A or ring B is, for example, (1–4C)alkylamino, such as methylamino, ethylamino, propylamino or butylamino.

A particular value for a di-alkylamino substituent which may be present on ring A or ring B is, for example, dimethylamino, diethylamino, methylpropylamino or dipropylamino.

A particular value for an alkylcarbamoyl substituent which may be present on ring A or ring B is, for example, N-methylcarbamoyl, N-ethylcarbamoyl or N-propylcarbamoyl.

A particular value for a di-alkylcarbamoyl substituent which may be present on ring A or ring B is, for example, N,N-dimethylcarbamoyl or N,N-diethylcarbamoyl.

A particular value for an alkoxycarbonyl substituent which may be present on ring A or ring B is, for example, methoxycarbonyl, ethoxycarbonyl or propoxycarbonyl.

A particular value for an alkylthio substituent which may be present on ring A or ring B is, for example, methylthio, ethylthio, propylthio, isopropylthio or butylthio.

A particular value for an alkylsulphinyl substituent which may be present on ring A or ring B is, for example, methylsulphinyl, ethylsulphinyl, propylsulphinyl, isopropylsulphinyl or butylsulphinyl.

A particular value for an alkylsulphonyl substituent which may be present on ring A or ring B is, for example, methylsulphonyl, ethylsulphonyl, propylsulphonyl, isopropylsulphonyl or butylsulphonyl.

A particular value for a halogeno substituent which may be present on ring A or ring B is, for example, fluoro, chloro or bromo.

A particular value for halogenoalkyl substituent which may be present on ring A or ring B is, for example, one which contains one, two or three halo groups selected from fluoro, chloro and bromo and the alkyl group is selected from methyl, ethyl, propyl, iso-propyl, butyl, isobutyl or sec-butyl. Thus, a particular value for a halogenoalkyl substitent will include, for example, trifluoromethyl.

The ring B may be attached to ring A so that ring B is ortho-, meta- or para- to the heterocyclic group. Thus, ring A may comprise a 1,2-phenylene, 1,3-phenylene or 1,4-phenylene moiety (optionally substituted as herein defined).

In general it is preferred, for example, that ring B is meta or para to the heterocyclic group, especially para. Thus, in general it is preferred, for example, that ring A comprises a 1,3-phenylene or 1,4-phenylene moiety, especially a 1,4-phenylene moiety (optionally substituted as herein defined).

In general it is preferred, for example, that $R^1$ is hydroxy and $R^2$ is hydrogen.

In general it is preferred, for example, that one or both of ring A or ring B is independently unsubstituted or substituted by one or more substituents selected from halogeno, hydroxy, nitro, (1–6C)alkyl, (1–6C)alkoxy, (1–6C)alkylthio, (1–6C)alkylsulphinyl, (1–6C)alkylsulphonyl and halogeno-(1–6C)alkyl.

In general, it is preferred that, ring A and ring B may be unsubstituted or may bear up to three substituents in total. For example, ring A may be unsubstituted, with ring B bearing up to three substituents; or ring A may bear a single substituent and ring B bear up to two substituents.

A more particular value for ring A is when it is unsubstituted. A more particular value for ring B is phenyl which bears a substituent at the 4-position selected from those hereinbefore defined.

Specific values for ring A include, for example, an unsubtituted 1,4-phenylene moiety. Specific values for ring B include, for example, phenyl, halophenyl (such as 4-fluorophenyl), alkoxyphenyl (such as 4-ethoxyphenyl) and hydroxyphenyl (such as 4-hydroxyphenyl).

In one embodiment of the present invention $R^1$ and $R^2$ are both hydrogen; and one or both of ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C) alkylsulphinyl, (1–6C)alkylsulphonyl and halogeno-(1–6C)alkyl.

Particular and preferred values for the various optional substituents for ring A and ring B are as above. As mentioned above, it is generally preferred that ring B is meta or para (especially para) to the heterocyclic moiety. Thus, it is generally preferred that ring A comprises a 1,3-phenylene or 1,4-phenylene moiety, especially a 1,4-phenylene moiety (optionally substituted as herein defined).

In a second embodiment of the present invention $R^1$ is hydroxy; $R^2$ is hydrogen; and one or both of ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl.

Particular and preferred values for the various optional substituents for ring A and ring B are those given above. As mentioned above, it is generally preferred that ring B is meta or para (especially para) to the heterocyclic moiety. Thus, it is generally preferred that ring A comprises a 1,3-phenylene or 1,4-phenylene moiety, especially a 1,4-phenylene moiety (optionally substituted as herein defined).

In a further embodiment of the present invention $R^1$ and $R^2$ are joined together so that $CR^1$–$CR^2$ is a double bond; and one or both of ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl] carbamoyl, N,N-di-[(1–6C)alkyl]carbamoyl, (1–6C) alkoxycarbonyl, (1–6C)alkylthio, (1–6C)alkylsulphinyl, (1–6C)alkylsulphonyl and halogeno-(1–6C)alkyl.

Particular and preferred values for the various optional substituents for rings A and B are those mentioned above. As mentioned above, it is generally preferred for example, that ring B is meta or para (especially para) to the heterocyclic moiety. Thus, it is generally preferred that ring A comprises a 1,3-phenylene or 1,4-phenylene moiety, especially a 1,4-phenylene moiety (optionally substituted as herein defined).

In a further embodiment of the present invention $R^1$ is hydroxy; $R^2$ is hydrogen; ring A is a 1,4-phenylene moiety; and one or both of ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl.

Many of the compounds of the present invention are novel and are provided as a further feature of the present invention.

In particular, according to the present invention there is also provided a compound of formula I (formula set out hereinafter together with the other chemical formulae referred to herein), or a pharmaceutically-acceptable salt thereof, wherein: $R^1$ is hydrogen or hydroxy; $R^2$ is hydrogen; or $R^1$ and $R^2$ are joined together so that $CR^1-CR^2$ is a double bond; ring B may be optionally unsubstituted or substituted by one or more substituents independently selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbamoyl, (1–6C)alkylthio, (1–6C)alkylsulphinyl, (1–6C)alkylsulphonyl and halogeno-(1–6C)alkyl; and ring A may be optionally unsubstituted or substituted by one or more substituents independently selected from amino, nitro, (1–6C)alkyl, (1–6C)alkylthio, (1–6C)alkylsulphinyl and (1–6C)alkylsulphonyl; but excluding the compound in which $R^1$ is hydroxy, $R^2$ is hydrogen, ring A is a 1,4-phenylene moiety, and ring A and ring B are both unsubstituted, and its pharmaceutically acceptable salts.

Particular, preferred and specific values include the appropriate values mentioned above.

Thus, for example, in one embodiment $R^1$ and $R^2$ are both hydrogen and ring A and ring B are as defined above; in a second embodiment $R^1$ is hydroxy and $R^2$ is hydrogen, and ring A and ring B are as defined above; and in a further embodiment $R^1$ and $R^2$ are joined together so that $CR^1-CR^2$ is a double bond, and ring A and ring B are as defined above.

In particular, it is generally preferred, for example, that ring B is meta- or para- (especially para-) to the heterocyclic group.

It is generally preferred, for example, that $R^1$ is hydroxy and $R^2$ is hydrogen.

Thus, in a particular embodiment, $R^1$ is hydroxy, $R^2$ is hydrogen, ring A is a 1,4-phenylene moiety and ring A and ring B are optionally substituted as hereinbefore defined.

More particular values for ring A include, for example, when ring A is unsubstituted or substituted by one or more substituents independently selected from nitro, (1–6C)alkyl, ((1–6C)alkylthio, (1–6C)alkylsulphinyl and (1–6C)alkylsulphonyl.

In particular, it is generally preferred, for example, that ring A is unsubstituted.

Thus in a further embodiment of the present invention there is provided a compound of formula I (formula set out hereinafter together with the other chemical formulae referred to herein), or a pharmaceutically-acceptable salt thereof, wherein: $R^1$ is hydrogen or hydroxy; $R^2$ is hydrogen; or $R^1$ and $R^2$ are joined together so that $CR^1-CR^2$ is a double bond; ring B may be optionally unsubstituted or substituted by one or more substituents independently selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkylthio, (1–6C)alkylsulphinyl and (1–6C)alkylsulphonyl; and ring A is unsubstituted.

Compounds of the invention which are of particular interest include the compounds described in the accompanying Examples (and their pharmaceutically-acceptable salts), and are hence provided as a further feature of the present invention.

A suitable pharmaceutically-acceptable salt of the present invention comprises an acid-addition salt derived from an inorganic or organic acid which provides a pharmaceutically-acceptable anion. Thus, examples of salts of the present invention include acid-addition salts with hydrochloric, hydrobromic, nitric, sulphuric, phosphoric, trifluoroacetic, citric, tartaric, succinic, maleic, fumaric or acetic acid. In addition, suitable pharmaceutically-acceptable salts include [where the compound of formula I is sufficiently acidic, for example where the compound of formula I bears an acidic substituent such as carboxy] those formed with a base which affords a pharmaceutically acceptable cation. Suitable bases include an alkali metal salt (such as a sodium or potassium salt), an alkaline earth metal salt (such as a calcium or magnesium salt), an ammonium salt or a salt with an organic base which affords a physiologically-acceptable cation such as a salt with methylamine, dimethylamine, triethylamine, piperidine or morpholine.

The compounds of the present invention may be obtained by standard procedures of organic chemistry already known to be applicable to the preparation of structurally analogous compounds. Such procedures for the preparation of the compounds of formula I, or pharmaceutically acceptable salts thereof, are provided as a further feature of the present invention and are illustrated by the following preferred processes in which the various generic radicals, for example, $R^1$ and $R^2$, have any of the meanings defined hereinbefore, and in which the rings A and B may be unsubstituted or substituted as hereinbefore defined.

Thus according to the present invention there is also provided a process for preparing a compound of formula I, or a pharmaceutically-acceptable salt thereof, which process comprises:

a) For those compounds of formula I in which $R^1$ is hydroxy and $R^2$ is hydrogen, reacting a compound of formula II, in which M is a metal atom or a derivative thereof, with quinuclidin-3-one.

In this reaction the organometalic compound II is reacted with quinuclidin-3-one. Suitable values for M include, for example, magnesium and lithium. In the case where M is magnesium it is conveniently present in the form of a derivative such as the group MgX where X is a halogen atom, such as iodo or bromo, so that the compound of formula II is a "Grignard reagent". The reaction is generally carried out in an inert solvent such as dry diethyl ether or tetrahydrofuran, with cooling at least during part of the reaction. For example, the reaction may be carried out at a temperature below 0° C., such as a temperature between 0° C. and −78° C.

The compounds of formula II may be prepared from a compound of formula IIa in which X is a halogen atom, such as iodo or bromo. The compound of formula IIa may be reacted directly with the metal M. For example in the case of magnesium, the Grignard reagent of formula II may be prepared by reaction of a compound of formula IIa (in which X is bromo or iodo) with magnesium turnings as is well known in the art. The desired Grignard reagent may also be prepared by a transmetallation reaction, for example by reaction of a compound of formula IIa with a different Grignard reagent, such as EtMgBr. Where M is lithium, the compound of formula IIa may be reacted with lithium in an inert solvent such as ether, or by reaction with a derivative such as an alkyl lithium derivative. In general it is preferred that an alkyllithium is used, with sec-butyl lithium being the preferred reagent. For preparation of compounds of formula II, suitable solvents include inert solvents such as diethylether and tetrahydrofuran. Conveniently, the reaction is carried out with cooling below 0° at least during part of the reaction.

The compounds of formula IIa are known or may be prepared by techniques well known in the chemical art. For example, they may be prepared by coupling two appropriately substituted phenyl rings using processes well known in the art, such as a process analogous to those described in (b) or (c) below.

b) For those compounds of formula I in which $R^1$ is hydrogen or hydroxy and $R^2$ is hydrogen, reacting a compound of formula III with a compound of formula IV wherein one of $Y^1$ and $Y^2$ is a halogen atom or a trifluoromethanesulphonyloxy group, and the other of $Y^1$ and $Y^2$ is a metal atom or a metal atom having suitable ligands, in the presence of a catalyst. Suitable values for $Y^1$ or $Y^2$ when halogen include, for example, chloro, bromo and iodo (especially bromo or iodo).

Suitable values for the metal atom include, for example, copper and lithium. Suitable values for a metal atom having suiatable ligands include, for example, those which contain a tin, boron, silicon, zirconium, aluminium, magnesium or mercury atom. Suitable ligands include, for example, alkyl groups (such as methyl, ethyl, propyl or butyl); halogen (such as fluoro, bromo or iodo); and hydroxy. Particular ligands include, for example, for tin, three substituents independently selected from (1–6C)alkyl (such as methyl, ethyl, propyl or butyl); for silicon a substituent selected from methyl and fluoro together with two fluoro atoms; for zirconium atom a halogeno group (such as fluoro, chloro, bromo or iodo) and two cyclopentadienyl radicals; for aluminium, two groups independently selected from (1–6C) alkyl (such as methyl, ethyl, propyl or butyl); for mercury atom a single group selected from a halogeno (such as fluoro, chloro, bromo or iodo), trifluoroacetyloxy or acetyloxy group; for magnesium, a halogeno group (such as fluoro, chloro, bromo or iodo); and for boron two groups independently selected from hydroxy, (1–4C)alkoxy (such as methoxy or ethoxy) and (1–6C)alkyl (such as methyl, ethyl, propyl or butyl). In the case of boron, the groups may, together with the boron atom to which they are attached, form a boroxin ring.

Suitable catalysts include, for example, a catalyst selected from a palladium(0), palladium(II), nickel(0) and nickel(II) catalyst, optionally in the presence of a radical initiator, and optionally in the presence of lithium chloride; and wherein when the metal is a silicon atom a source of fluoride ion (for example, an alkali metal halide such as sodium or potassium fluoride, or a tetra-alkylammonium fluoride such as tetramethylammonium or tetrabutylammonium fluoride) is optionally present.

Particularly suitable leaving groups are the groups —Sn(Bu)$_3$, and —B(OH)$_2$.

Particular catalysts include, for example, tetrakis(triphenylphosphine)nickel(0), bis(triphenylphosphine)nickel(II) chloride, nickel(II)chloride, palladium(II) chloride, bis(triphenylphosphine)palladium(II) chloride, bis(triphenylphosphine)phenylpalladium iodide and tetrakis(triphenylphosphine)palladium(0).

A suitable radical initiator is, for example, azo (bisisobutyronitrile).

The process is generally performed in the presence of a suitable solvent or diluent, for example, a hydrocarbon, such as toluene or xylene, or an ether, such as dioxan or tetrahydrofuran, and at a temperature in the range, for example, 20°–150° C. The process is also preferably carried out in the presence of a radical initiator.

Compounds of the formula III are known or may be obtained by analogy therewith or, for example, by reaction of a compound of the formula $Y^1$.Hal. wherein $Y^1$ is the metal atom (defined above) and Hal. is a halogeno group such as chloro, bromo or iodo, with a Grignard reagent or phenyllithium compound derived, using standard procedures, from a compound of the formula IIIa wherein the phenyl ring is optionally substituted as defined above for ring B and W is a halogeno group such as chloro, bromo or iodo. The reaction is generally carried out in a solvent such as tetrahydrofuran or ether, or a mixture thereof, and at a temperature of –78° C. to 25° C. In the case where the group which comprises a boron atom having ligands selected from alkoxy and hydroxy, the compounds of formula III may also be prepared by reaction of a trialkylboronate of the formula B(OR)$_3$ wherein R is a (1–6C)alkyl group with a Grignard reagent or phenyllithium compound derived, using standard procedures, from a compound of the formula IIIa wherein the phenyl ring is optionally substituted as defined above for ring B and W is a halogeno group such as chloro, bromo or iodo. The reaction is generally carried out in a solvent such as tetrahydrofuran or ether, or a mixture thereof, and at a temperature of –78° C. to 25° C. The compounds of formula III wherein the ligands attached to boron are alkoxy can be converted to those in which the ligands are hydoxy using standard techniques. The boroxin derivatives may be prepared from the latter compounds by dehydration using standard procedures.

The compounds of formula IIIa are known or may be obtained using standard procedures of organic chemistry. @@The compounds of formu IV are known (from, for example EP 412,797) or may be prepared using standard procedures of organic chemistry. For example compounds of formula IV may be prepared from compounds of formula IVa and quinuclidin-3-one in an analgous manner to the preparation of compounds of formula I using process (a). The hydroxy group generated may be removed by hydrogenolysis or by dehydration to yield a double bond which may be reduced by, for example, catalytic hydrogenation. It may be convenient to carry out the Grignard reaction with X as a group which does not interfere with the Grignard reaction and which can be converted into a halogen atom folowing the Grignard reaction.

c) for those compounds of formula I in which $R^1$ is hydrogen or hydroxy and $R^2$ is hydrogen, reacting a compound of formula IV in which $Y^2$ is a halogeno group with a compound of formula IIIa in which W is a halogeno group, in the presence of a catalyst.

Suitable values for W and $Y^2$ in formulae IIIa and IV include chloro and bromo and iodo.

Suitable catalysts include copper, copper bronze or copper (II)oxide, or transition metal complexes such as those mentioned under (b) above.

A particularly suitable catalyst is, for example, copper, copper bronze or copper(II)oxide. The coupling of a compound of formula IV and V using such a catalyst is known as an "Ullmann" reaction and is well known to those skilled in the art.

Suitable coupling conditions include heating the compounds of formula IV and IIIa with the copper catalyst at a temperature of up to about 225° C. Conveniently, the reaction may be carried out in the presence of sand.

The reaction may also be carried out in the presence of a solvent such as quinoline or dimethylformamide, in which case the reaction will be carried out with heating, conveniently at reflux.

d) For compounds of formula I in which $R^1$ and $R^2$ are both hydrogen, reducing a compound of formula I in which $R^1$ and $R^2$ are joined together so that $CR^1-CR^2$ is a double bond.

The reduction may be carried out, for example, by catalytic hydrogenation, or by reaction with a suitable reducing agent.

Suitable reaction conditions include, for example, catalytic hydrogenation using a catalyst which comprises a noble metal. Particular catalysts include palladium, platinium and nickel (especially when in the finely divided state known as Raney nickel), and catalysts in which the noble metal is supported on an inert carrier such as carbon. A specific example of a supported catalyst is Pd/C. The reduction is conveniently carried out in a solvent of, for example, an alcohol such as ethanol, and at (or near) ambient temperature and optionally under pressure.

Further suitable reaction conditions include, for example, reduction with a borane such as diborane. The reaction is generally carried out in an inert solvent of, for example, tetrahydrofuran or methyl t-butyl ether at, for example 0°–60° C. It may be preferable to cool the reaction below ambient temperature (eg to about 0° C.) during the reduction. The borane generated may be hydolysed by treatment with an organic acid such as acetic acid, which hydrolysis may be carried out at 0°–60° C., and may be accelerated by heating (eg refluxing).

e) For compounds of formula I in which R1 and R2 are joined together so that $CR^1-CR^2$ is a double bond, dehydrating a compound of formula I in which $R^1$ is hydroxy.

The dehydration may be carried out using an acid such as sulphuric acid (eg concentrated sulphuric acid), or p-toluene sulphonic acid. The reaction is conveniently carried with heating, and conveniently an inert solvent is employed. For example, the reaction may be carried out using sulphuric acid at temperatures of about 70°–130° C.; using p-toluenesulphonic acid in a hydrocarbon solvent of, for example, toluene or xylene at ambient temperature to relux, and preferably at reflux. The dehydration may also be carried out using trifluoroacetic acid in an inert solvent such as dichloromethane (at ambient temperature to reflux temperature).

f) For compounds of formula I in which R1 and R2 are joined together so that $CR^1-CR^2$ is a double bond, treating a compound of formula V in which X is a leaving group with a base.

Suitable values for X include, for example, halogen such as chloro, bromo or iodo, or a methylsulphonyloxy or toluenesulphonyloxy group.

Suitable baes include hydroxide (such as potassium or sodium hydroxide), and alkoxides (such as potassium t-butoxide or sodium ethoxide).

The reaction is conveniently carried out in the presence of a solvent, preferably a polar organic solvent. Suitable solvents include, for example, an alcohol (such as ethanol), or aprotic solvents such as dimethylformamide or N-methylpyrrolidone.

The reaction may be carried out at ambient temperature or at an elevated temperature, such as at a temperature between ambient and the relux temperature of the reaction mixture.

The compounds of formula V may be prepared from a compound of formula I in which R1 is hydroxy. For example, where X is halogen the compound of formula I in which R1 is hydroxy may be reacted with the appropriate phosphorus halide (eg $PCl_5$, $PBr_3$ or $PI_3$), or where X is chloro, by reaction with thionyl chloride. The compound of formula I in which R1 is hydroxy may be reacted with mesyl chloride to give the compound in which X is methylsulphonyloxy; and with tosyl chloride to give X is toluene sulphonyloxy.

g) For compounds of formula I in which $R^1$ and $R^2$ are both hydrogen, by dehydroxylation of a compound of formula I in which $R^1$ is hydroxy.

Suitable reaction conditions are those mentioned with reference to catalytic hydrogenation under (d) above.

The reaction may also be accomplished using, for example trifluoroacetic acid and $Et_3SiH$, conveniently at a temperature between ambient temperature and reflux (eg at about 50° C.).

It will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups for hydroxy include, for example, silyl groups such as trimethylsilyl or t-butylsilyl, tetrahydropyranyl and esterifing groups such as a methyl or ethyl ester; and for amino groups include benzyloxycarbonyl and t-butoxycarbonyl. Carboxy groups may be protected in a reduced form such as in the form of the corresponding protected alcohol, which may be subsequently oxidised to give the carboxy group. The protecting groups may be removed at any convenient stage in the synthesis using conventional techniques well known in the chemical art.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

As mentioned previously, the compounds of the formula I (and their pharmaceutically-acceptable salts) are inhibitors of the enzyme squalene synthetase. Thus the compounds of the present invention inhibit cholesterol biosynthesis by inhibition of de novo squalene production.

The beneficial pharmacological properties of the compounds of the present invention may be demonstrated using one or more of the following techniques.

(a) Inhibition of Squalene Synthetase

In this test, the ability of a compound to prevent the formation of squalene from a radioactive substrate (tritiated farnesyl pyrophosphate) is assessed.

The test compound is incubated at a concentration of 25 micromolar in 200 µl of a buffered solution containing potassium phosphate (50 mM), MgCl$_2$ (4.95 mM), KF (9.9 mM), NADPH (0.9 mM) and rat liver microsomal protein (20 µg). Rat liver microsomes are prepared by the method described in published European Patent Application No. 324,421 and stored in liquid nitrogen prior to assay. Assay vials are kept at 37° C. throughout the incubation.

The reaction is started with the addition of the substrate (1-[$^3$H]-farnesyl pyrophosphate), final concentration 20 µM, and stopped after 15 minutes reaction time with the addition of 50 µl of 4% KOH. The reaction products are separated from unreacted substrate after application to a C-18 octadecyl lccBond column (Analytichem Int product No. 617101). An aqueous fraction is eluted with 250 µl of 0.1M KOH. Squalene is then eluted with 1.0 ml 10% ethylacetate in hexane and radioactivity determined. The difference in radioactivity in the presence and absence of the test compound is used to determine the level of inhibition. If the test compound inhibits at greater than about 70% at 25 micromolar, it is generally re-tested at 25 and 2.5 micromolar. The IC$_{50}$ (concentration which results in a 50% inhibition of squalene production), of the test compound can be determined by testing the compound at several, for example five, concentrations predicted from the two concentration results. The IC$_{50}$ can then be determined from a plot of percentage inhibition against concentration of test compound.

In general, compounds of formula I show significant inhibition in the above test at a concentration in the range of about 0.001 to 25 µM.

By way of illustration of the squalene synthetase inhibitory properties of the compound of formula I, described in Example 3 below gave an IC$_{50}$ of $6\times10^{-7}$M.

(b) Acute Rat Cholesterol Synthesis Assay

This is an acute in vivo test in the rat to measure de novo hepatic cholesterol synthesis from exogenously administered $^{14}$C-acetate.

Female rats (35–55 g) are housed in reverse lighting conditions (red light from 0200h–1400h) for a period of about 2 weeks prior to test. Animals are allowed free access to chow and drinking water throughout this period. At test, animals should weigh 125–150 g.

Test compounds may be administered by oral gavage, dissolved or suspended in 0.5% polysorbate, or by ip or iv dosing. Control animals receive vehicle alone. After 1 hour the rats are injected ip with 25 µCi [2-$^{14}$C]-acetate (NEN DUPONT, specific activity, 45–60 mCi/mmol NEC-085H, or AMERSHAM specific activity, 50–60 mCi/mmol CFA 14) in a volume of 0.25 ml saline (100 µCi/ml). After a further hour, rats are terminally anaesthetised with halothane and a blood sample obtained from the abdominal vena cava.

1 ml of plasma is lyophilised and then saponified in 2 ml ethanolic KOH (1 part 33% KOH, 9 parts ethanol) at 75° C. for 2 hours. After addition of an equal quantity of water, non-saponifiable lipids are extracted with two 5 ml volumes of hexane. The hexane extracts are evaporated to dryness and the residues dissolved in ethanol to determine cholesterol specific radioactivity. ED$_{50}$ values can be determined in the standard way.

In general, compounds of formula I show activity in the range of about 0.1 to 100 mg/kg.

By way of illustration, the compound described in Example 6 below gave an ED$_{50}$ of 8 mg/kg.

No overt toxicity was detected when compounds of the formula I were administered at several multiples of their minimum inhibitory dose or concentration.

As mentioned previously, the compounds of the present invention are squalene synthetase inhibitors and hence possess the property of inhibiting cholesterol biosynthesis. Thus the compounds of the present invention will be useful in treating diseases or medical conditions in which an inhibition of squalene synthetase is desirable, for example those in which a lowering of the level of cholesterol is blood plasma is desirable. In particular, the compounds of the present invention will be useful in treating hypercholesterolemia and/or ischaemic diseases associated with atheromatous vascular degeneration such as atherosclerosis.

When used in the treatment of diseases and medical conditions in which an inhibition of cholesterol biosynthesis is desired, for example in the treatment of hypercholesterolemia or atherosclerosis, it is envisaged that a compound of formula I (or a pharmaceutically acceptable salt thereof) will be administered orally, intravenously, or by some other medically acceptable route so that a dose in the general range of, for example, 0.01 to 10 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating.

such as an enteric coating (for example, one based on cellulose acetate phthalate), to minimise dissolution of the active ingredient of formula I (or a pharmaceutically-acceptable salt thereof) in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease, such as β-blockers, ACE inhibitors and/or calcium antagonists.

The compounds of the present invention may also find utility as antifungal agents, and so the present invention also provides a method of treating fungal infections which comprises administration to an a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

The invention will now be illustrated by the following non-limiting Examples in which, unless otherwise stated:

(i) evaporations were carried out by rotary evaporation in vacuo;
(ii) operations were carried out at room temperature, that is in the range 18°–26° C.;
(iii) yields are given for illustration only and are not necessarily the maximum attainable by diligent process development;
(iv) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;
(v) all end-products were characterised by microanalysis, NMR and/or mass spectroscopy; and
(vi) conventional abbreviations are used for individual radicals and recrystallisation solvents, for example, Me=methyl, Et=ethyl, Pr=Propyl, Pr$^i$=isopropyl, Bu=butyl, Bu$^i$=isobutyl, Ph=phenyl; EtOAc=ethyl acetate, Et$_2$O=diethyl ether, MeCN=acetonitrile, MeOH= methanol, EtOH=ethanol, Pr$^i$OH=2-propanol, H$_2$O= water.

EXAMPLE 1

A solution of sec-butyllithium in cyclohexane (100 ml, 1.3M) was added dropwise with stirring to a solution of 4-bromobiphenyl (25 g) in dry tetrahydrofuran (240 ml) under an argon atmosphere at −78° C. The mixture was stirred for 5 minutes and a solution of quinuclidin-3-one (12 g) in dry tetrahydrofuran (100 ml) added during 20 minutes. Stirring was continued at −78° C. for 30 minutes and the mixture allowed to reach room temperature over 2 hours. 2M Hydrochloric acid (225 ml) was added keeping the reaction temperature below 10° C. The aqueous layer was separated and washed with diethyl ether (2×300 ml) before the addition of excess sodium hydroxide solution (density 1.35 g/cm$^3$) to pH14. The mixture was extracted with ethyl acetate which had been heated to 50° C. and the ethyl acetate phase separated, dried (Na$_2$SO$_4$) and evaporated to yield a colourless solid which crystallised from ethyl acetate to give 3-(biphenyl-4-yl)-3-hydroxyquinuclidine (11.0 g) m.p. 165°–166° C.; microanalysis, found: C, 81.1; H, 7.5; N, 5.2%; C$_{19}$H$_{21}$NO 0.1H$_2$O requires: C, 81.1; H, 7.5; N, 5.0%; NMR (CDCl$_3$/CD$_3$CO$_2$D): 1.7–1.9(3H, m.), 2.5(1H, m), 2.5–2.7(1H, m), 3.2–3.5(4H, m), 3.7(1H, dd), 4.0(1H, dd) and 7.3–7.7(9H, m); m/z 279 (M$^+$).

EXAMPLE 2

A solution of 4-bromobiphenyl (11.8 g) in dry tetrahydrofuran (60 ml) and bromine (3 drops) were added to stirred magnesium turnings (1.18 g) and the mixture heated under reflux for 70 minutes. A solution of quinuclidin-3-one (3.65 g) in dry tetrahydrofuran (25 ml) was added dropwise to the mixture at 10° C. and the reaction mixture heated under reflux for 90 minutes. Aqueous ammonium chloride (14 g in 56 ml of water) was added dropwise to the mixture and the mixture extracted with diethyl ether. The ether extract was dried (Na$_2$SO$_4$) and evaporated to give a residue which was crystallised from ethyl acetate to give 3-(biphenyl-4-yl)-3-hydroxyquinuclidine (1.4 g) as a colourless solid, m.p. 180°–182° C., microanalysis, found: C, 81.7; H, 7.5; N, 5.0%; C$_{19}$H$_{21}$NO requires: C, 81.8; H, 7.5; N, 5.0%. This material was identical to that in Example 1 except that it was a higher melting polymorphic form.

EXAMPLE 3

Using a similar procedure to that in Example 1 but using 3-bromobiphenyl as starting material (in place of 4-bromobiphenyl), there was obtained 3-(biphenyl-3-yl)-3-hydroxyquinuclidine (33% yield). m.p. 165°–166° C., microanalysis, found: C, 81.1; H, 7.5; N, 5.2%; C$_{19}$H$_{21}$NO 0.1H$_2$O requires: C, 81.1; H, 7.5; N, 5.0%; NMR (CDCl$_3$/CD$_3$CO$_2$D) 1.7–1.95(3H, m), 2.5–2.7(2H, m), 3.3–3.6(4H, m), 3.7(1H, dd), 4.1(1H, dd), 7.3–7.7(8H, m) and 7.8(1H, s); m/z 280 (M+H).

EXAMPLE 4 p-Toluenesulphonic acid (9.76 g) and 3-(biphenyl-4-yl)-3-hydroxyquinuclidine (4.7 g) were heated under reflux in toluene (300 ml) for 2 hours using a Dean and Stark water separator. The toluene was evaporated and the residue dissolved in 1N sodium hydroxide solution (125 ml). The aqueous mixture was extracted with ethyl acetate, the ethyl acetate separated, washed with brine, dried (Na$_2$SO$_4$) and concentrated to 60 ml. Excess of saturated ethereal hydrogen chloride was added and the precipitated solid crystallised from methanol/ethyl acetate to give as a colourless solid 3-(biphenyl-4-yl)-2,3-dehydroquinuclidine hydrochloride (3.7 g) m.p. 263°–265° C., microanalysis, found: C, 76.2; H, 6.6; N, 4.7%; C$_{19}$H$_{19}$N.HCl requires: C, 76.6; H, 6.8; N, 4.7%;. NMR: ([CD$_3$]$_2$SO) 1.6–1.8(2H, m), 1.95–2.15(2H, m), 2.9–3.1(2H, m), 3.5–3.7(3H, m), 7.1(1H, d), 7.3–7.5 (3H, m) and 7.6–7.8(6H, m); m/z 262 (M+H).

EXAMPLE 5

3-(Biphenyl-4-yl)-2,3-dehydroquinuclidine hydrochloride (260 mg) in absolute ethanol (25 ml) was hydrogenated at atmospheric pressure for 4 hours over a catalyst of 10% palladium on carbon. The catalyst was removed by filtration and the alcohol evaporated. The residue was crystallised from methanol/ethyl acetate to give as a colourless solid 3-(biphenyl-4-yl)quinuclidine hydrochloride (175 mg) m.p.

248°–249° C., microanalysis, found: C. 69.8; H. 7.8; N. 4.3%; $C_{19}H_{21}N.HCl$ $1.5H_2O$ requires: C. 69.8; H. 7.7; N. 4.3%;; NMR: ($[CD_3]_2SO/CD_3CO_2D$) 1.6–1.8(1H, m), 1.9–2.2(3H, m), 3.1–3.8(8H, m) and 7.3–7.7(9H, m); m/z 264 (M+H).

EXAMPLE 6

Using a similar procedure to that described in Example 1 but using 4-bromo-4'-fluorobiphenyl as starting material in place of 4-bromobiphenyl, there was obtained 3-[4'-fluorobiphenyl-4-yl]-3-hydroxyquinuclidine (36% yield), m.p. 172°–173° C., microanalysis, found: C, 75.7; H, 6.7; N, 4.9%; $C_{19}H_{20}F$ NO $0.25H_2O$ requires: C. 75.6; H. 6.8; N. 4.6%; NMR ($[CD_3]_2SO$): 1.2–1.5(3H, m), 1.9–2.0(1H, m), 2.1–2.2(1H, m), 2.6–3.4(6H, m), 5.1(1H, s), 7.2–7.3(2H, m), 7.6(4H, s), 7.6–7.7(2H, m); m/Z 298 (M+H).

EXAMPLE 7

Using a similar procedure to that described in Example 1 but using 4-bromo-4'-ethoxybiphenyl as starting material in place of 4-bromobiphenyl, there was obtained 3-[4'-ethoxybiphenyl-4-yl]-3-hydroxyquinuclidine (55% yield), m.p. 199°–200° C., microanalysis, found: C, 77.7; H, 7.9; N, 4.4%; $C_{21}H_{25}NO_2$ requires: C, 78.0; H, 7.8; N, 4.3%; NMR ($[CD_3]SO/CD_3COOD$): 1.3–1.4(3H, t), 1.5–1.7(1H, m), 1.8–1.9(2H, m), 2.4–2.5(2H, s), 3.1–3.4(4H, m), 3.4–3.9 (2H, d of d), 4.0–4.1(2H, q), 7.0(2H, d), 7.5–7.7(6H, m); m/Z 324 (M+H).

The 4-bromo-4'-ethoxybiphenyl used as starting material was prepared as follows:

4-Bromo-4'-hydroxybiphenyl (2.49 g) was added over 30 minutes to a stirred suspension of sodium hydride (0.42 g of 60% dispersion in mineral oil) in dimethylformamide (10 ml) whilst keeping the temperature of the reaction mixture below 10° C. The reaction mixture was stirred at a temperature below 10° C. for a futher 5 minutes. Ethyl iodide (1.87 g) was added over 10 minutes and stirring continued at room temperature for 2 hours. Water (200 ml) was added to the mixture and the mixture extracted with diethyl ether (3×50 ml). The ether extracts were combined, washed with 1M sodium hydroxide solution (50 ml) and brine (50 ml), dried ($MgSO_4$) and evaporated to give a residue which was crystallised from hexane to give, as a colourless solid, 4-bromo-4'-ethoxybiphenyl (2.15 g), m.p. 139° C.; NMR ($CDCl_3$): 1.4(3H, t), 4.0–4.1 (2H, q), 6.9(2H, d) and 7.35–7.55(6H, m).

EXAMPLE 8

Using a similar procedure to that described in Example 4 but using 3-(biphenyl-3-yl)-3-hydroxy-quinuclidine as starting material in place of 3-(biphenyl-4-yl)-3-hydroxyquinuclidine, there was obtained 3-(biphenyl-3-yl)-2,3-dehydroquinuclidine hydrochloride (84% yield), m.p. 244°–245° C., microanalysis, found: C, 75.6; H, 6.6; N, 4.8%; $C_{19}H_{19}N.HCl.0.25H_2O$ requires: C, 75.5; H, 6.8; N, 4.6%; NMR ($[CD_3]_2SO/CD_3COOD$): 1.7–2.2(4H, m), 3.0–3.2(2H, m), 3.5–3.8(3H, m), 7.2–7.9(10H, m); m/Z 262(M+H).

EXAMPLE 9

Using a similar procedure to that described in Example 5 but using 3-(biphenyl-3-yl)-2,3-dehydroquinuclidine hydrochloride as starting material in place of 3-(biphenyl-4-yl)-2,3-dehydroquinuclidine hydrochloride, there was obtained 3-(biphenyl-3-yl)quinuclidine hydrochloride (62% yield) m.p. 178°–180° C., microanalysis, found: C, 72.4; H, 7.3; N, 4.5%; $C_{19}H_{21}N.HCl.0.75H_2O$ requires: C, 72.8; H, 7.5; N, 4.5%; NMR ($[CD_3]^2SO]//CD_3COOD$): 1.6–2.3(5H, m), 3.2–3.8(7H, m), 7.3–7.7(9H, m); m/Z 264 (M+H).

EXAMPLE 10

A solution of sec-butyllithium in cyclohexane (7.4 ml, 1.3M) was added dropwise, with stirring, to a solution of 4-bromo-4'-(tert-butyldimethylsilyloxy)biphenyl (2.9 g) in dry tetrahydrofuran (30 ml) under an atmosphere of argon at −78° C. The mixture was stirred for 5 minutes and a solution of quinuclidin-3-one (0.9 g) in dry tetrahydrofuran (12 ml) was then added over a period of 2 minutes. The mixture was stirred at −78° C. for a further 30 minutes and the mixture then allowed to warm to room temperature over 2 hours. Aqueous 2M hydrochloric acid (18 ml) was added to the reaction mixture, whilst keeping the temperature of the reaction mixture below 10° C. The aqueous layer was separated and washed with diethyl ether (2×20 ml) before the addition of excess sodium hydroxide solution (density 1.35 g/cm$^3$) to pH 14. The mixture was extracted with warm ethyl acetate (50° C.) and the ethyl acetate phase separated, dried ($Na_2SO_4$) and evaporated. The residue was dissolved in dry tetrahydrofuran (20 ml) and added to a solution of tetrabutyl ammonium fluoride in tetrahydrofuran (1.6 ml, 1.0M). The mixture was stirred at room temperature for 2 hours. The tetrahydrofuran was evaporated, an excess of saturated ethereal hydrogen chloride solution was added to precipitate a solid which was crystallised from methanol/ethyl acetate to give as a colourless solid, 3-(4'-hydroxybiphenyl-4-yl)-3-hydroxy-quinuclidine hydrochloride (0.93 g), m.p. 270°–271° C., microanalysis, found: C, 66.5; H, 6.5; N, 4.1%; $C_{19}H_{21}NO_2.HCl.0.66H_2O$ requires: C, 66.5; H, 6.8; N, 4.1%; NMR ($[CD_3]_2SO$): 1.4–1.6(1H, m), 1.7–1.9(2H, m), 2.3–2.4(2H, m), 3.1–3.4(5H, m), 3.8–3.9(1H, d), 5.9(1H, s), 6.9–7.5(4H, d of d), 7.6(4H, s), 9.6(1H, s); m/Z 296 (M+H).

The 4-bromo-4'-(tert-butyldimethylsilyloxy)biphenyl used as starting material was prepared as follows:

tert-Butyldimethylsilyl chloride (1.8 g) was added over 30 minutes to a stirred solution of 4-bromo-4'-hydroxybiphenyl (2.49 g) and imidazole (1.63 g) in dimethylformamide (15 ml) whilst keeping the temperature of the reaction mixture below 10° C. The reaction mixture was stirred at room temperature for 18 hours. Diethyl ether (225 ml) was added, the ether washed with saturated sodium hydrogen carbonate solution (3×60 ml) and brine (100 ml), dried ($MgSO_4$) and evaporated to yield, as a colourless oil, 4-bromo-4'-(tert-butyldimethylsilyloxy)biphenyl (3.2 g); NMR ($CDCl_3$): 0.2(6H, s), 1.0(9H, s), 6.8–6.9(2H, d), 7.3–7. 4(4H, m) and 7.45–7.55(2H, d).

EXAMPLE 11

A racemic (±) mixture of 3-(biphenyl-4-yl)-3-hydroxyquinuclidine was resolved by chromatography on a chiral cell OD column using a 70:30:0.2 mixture (by volume) of hexane/propan-2-ol/triethylamine as eluant to give the separate enantiomers which were crystallised from butan-2-one to give as crystalline solids (+) 3-(biphenyl-4-yl)-3-hydroxyquinuclidine, m.p. 158°–159° C.; $[\alpha]^{22}_D$=+32.0° (c=3.4 mg/ml in methanol), and (−) 3-(biphenyl-4-yl)-3-hydroxyquinuclidine, m.p. 159°–160° C.; $[\alpha]^{22}_D$=−31.2° (c=3.3 mg/ml in methanol).

EXAMPLE 12

Using a similar separation procedure to that described in Example 11, but using a racemic mixture of 3-(biphenyl-4-yl)-quinuclidine hydrochloride as starting material in place of racemic (±) 3-(biphenyl-4-yl)-3-hydroxyquinuclidine, there was obtained (+) 3-(biphenyl-4-yl)quinuclidine, m.p. 87°–88° C.; microanalysis, found: C, 83.6; H, 8.1; N, 5.0%; $C_{19}H_{21}N.0.5H_2O$ requires: C, 83.8; H, 8.1; N, 5.1%; $[\alpha]^{22}_D$=+38.2° (c=3.3 mg/ml in methanol), and (−) 3-(biphenyl-4-yl)-quinuclidine, m.p. 85°–86° C.; $[\alpha]^{22}_D$=−30.4° (c=3.35 mg/ml in methanol).

EXAMPLE 13

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

|  | mg/tablet |
| --- | --- |
| (a) Tablet I |  |
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |
| (b) Tablet II |  |
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III |  |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule |  |
| Compound Z* | 10 |
| Lactose Ph.Eur. | 488.5 |
| Magnesium stearate | 1.5 |

Note
*The active ingredient Compound Z is a compound of formula I, or a salt thereof, for example a compound of formula I described in any of the preceding Examples.
The tablet compositions (a)–(c) may be enteric coated by conventional means, for example, with cellulose acetate phthalate.

The tablet compositions (a)–(c) may be enteric coated by conventional means, for example, with cellulose acetate phthalate.

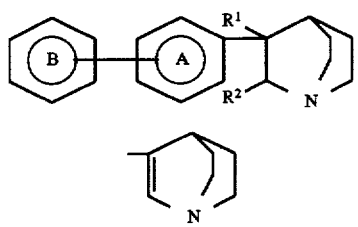

I

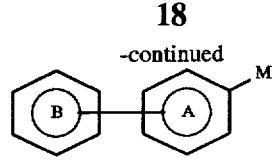

II

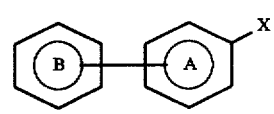

IIa

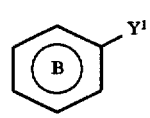

III

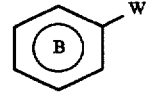

IIIa

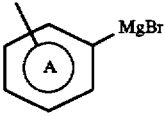

IVa

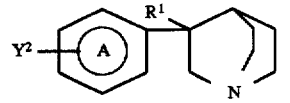

IV

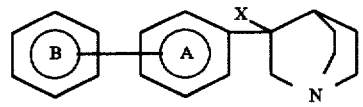

V

It is claimed:

1. A biphenylylquinuclidine compound of the formula:

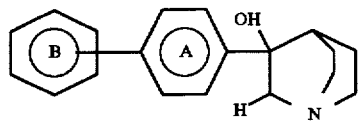

or a pharmaceutically-acceptable salt thereof, wherein ring B may be optionally unsubstituted or substituted by one or more substituents independently selected from halogeno, hydroxy, amino, nitro, cyano, carboxy, carbamoyl, (1–6C) alkyl, (1–6C)alkoxy, (1–6C)alkylamino, di-[(1–6C)alkyl] amino, N-[(1–6C)alkyl]carbamoyl, N,N-di-[(1–6C)alkyl] carbamoyl, (1–6C)alkoxycarbamoyl, (1–6C)alkylthio, (1–6C)alkylsulphinyl, (1–6C)alkylsulphonyl and halogeno-(1–6C)alkyl; and ring A may be optionally unsubstituted or substituted by one or more substituents independently selected from amino, nitro, (1–6C)alkyl, (1–6C)alkylthio, (1–6C)alkylsulphinyl and (1–6C)alkylsulphonyl; but excluding the compound and its pharmaceutically acceptable salts in which ring A and ring B are both unsubstituted.

2. The compound of claim 1 wherein ring B is selected from the group consisting of phenyl, 4-hydroxyphenyl, 4-ethoxyphenyl and 4-fluorophenyl.

3. The compound according to claim 1, wherein the compound is selected from the group consisting of 3-(4'-fluorobiphenyl-4-yl)-3-hydroxy-quinuclidine;
3-(4'-ethoxybiphenyl-4-yl)-3-hydroxy-quinuclidine; and
3-(4'-hydroxybiphenyl-4-yl)-3-hydroxy-quinuclidine;

or a pharmaceutically acceptable salt thereof.

4. A pharmaceutical composition which comprises a compound as claimed in any one of claims 1, 2 and 3, together with a pharmaceutically acceptable diluent or carrier.

5. A method of inhibiting squalene synthetase in a warm blooded animal in need thereof, comprising administering to said animal a squalene synthetase inhibitory effective amount of a biphenylquinuclidine compound of the formula:

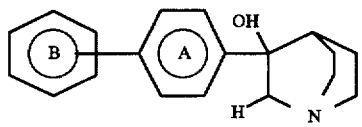

or a pharmaceutically-acceptable salt thereof, wherein one or both ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl.

6. The method of claim 5 wherein:

one or both ring A and ring B may be optionally unsubstituted or independently substituted by one or more substituents selected from fluoro, chloro, bromo, hydroxy, amino, nitro, cyano, carboxy, carbamoyl, methyl, ethyl, propyl, isopropyl, butyl, isobutyl, sec-butyl, methoxy, ethoxy, propoxy, isopropoxy, butoxy, methylamino, ethylamino, propylamino, butylamino, dimethylamino, diethylamino, methylpropylamino, dipropylamino, N-methylcarbamoyl, N-ethylcarbamoyl, N-propylcarbamoyl, N,N-dimethylcarbamoyl, N,N-diethylcarbamoyl, methoxycarbonyl, ethoxycarbonyl, propoxycarbonyl, methylthio, ethylthio, propylthio, isopropylthio, butylthio, methylsulphinyl, ethylsulphinyl, propylsulphinyl, isopropylsulphinyl, butylsulphinyl, methylsulphonyl, ethylsulphonyl, propylsulphonyl, isopropylsulphonyl, butylsulphonyl, or a halogenoalkyl group which comprises a methyl, ethyl, propyl, isopropyl, butyl, isobutyl or sec-butyl group having one, two or three halo groups selected from fluoro, chloro and bromo.

7. The method of claim 5 or 6 wherein ring B is selected from the group consisting of phenyl, 4-hydroxyphenyl, 4-ethoxyphenyl and 4-fluorophenyl.

8. The method according to claim 5 or 6, wherein the compound is selected from the group consisting of 3-(biphenyl-4-yl)-3-hydroxy-quinuclidine;
3-(4'-fluorobiphenyl-4-yl)-3-hydroxy-quinuclidine;
3-(4'-ethoxybiphenyl-4-yl)-3-hydroxy-quinuclidine; and
3-(4'-hydroxybiphenyl-4-yl)-3-hydroxy-quinuclidine;

or a pharmaceutically acceptable salt thereof.

9. A method of lowering the level of cholesterol in blood plasma of a warm blooded animal in need thereof, said method comprising administering to said animal a blood plasma cholesterol lowering effective amount of a compound of the formula:

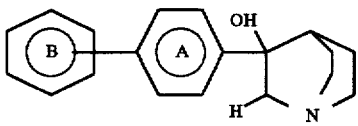

or a pharmaceutically acceptable salt thereof, wherein one or both ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl.

10. The method of claim 9 wherein ring B is selected from the group consisting of phenyl, 4-hydroxyphenyl, 4-ethoxyphenyl and 4-fluorophenyl.

11. The method according to claim 9, wherein the compound is selected from the group consisting of 3-(biphenyl-4-yl)-3-hydroxy-quinuclidine;
3-(4'-fluorobiphenyl-4-yl)-3-hydroxy-quinuclidine;
3-(4'-ethoxybiphenyl-4-yl)-3-hydroxy-quinuclidine; and
3-(4'-hydroxybiphenyl-4-yl)-3-hydroxy-quinuclidine;

or a pharmaceutically acceptable salt thereof.

12. A method of treating hypercholesterolemia or atheromatous vascular degeneration in a warm blooded animal, said method comprising administering to said animal in need thereof an effective amount of a compound of the formula:

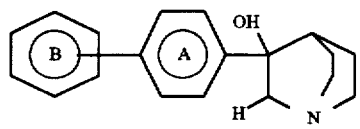

or a pharmaceutically acceptable salt thereof, wherein one or both ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl.

13. The method of claim 12 wherein ring B is selected from the group consisting of phenyl, 4-hydroxyphenyl, 4-ethoxyphenyl and 4-fluorophenyl.

14. The method according to claim 12, wherein the compound is selected from the group consisting of 3-(biphenyl-4-yl)-3-hydroxy-quinuclidine;
3-(4'-fluorobiphenyl-4-yl)-3-hydroxy-quinuclidine;
3-(4'-ethoxybiphenyl-4-yl)-3-hydroxy-quinuclidine; and
3-(4'-hydroxybiphenyl-4-yl)-3-hydroxy-quinuclidine;

or a pharmaceutically acceptable salt thereof.

15. A method of treating fungal infections in a warm blooded animal, said method comprising administering to said animal in need thereof an effective amount of a compound of the formula:

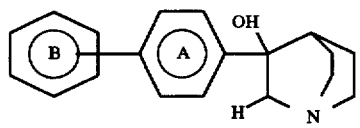

or a pharmaceutically acceptable salt thereof, wherein one or both ring A and ring B may be optionally unsubstituted or independently substituted by one or more substituents selected from halogeno, hydroxy, amino, nitro, cyano, carboxy, carbamoyl, (1–6C)alkyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl.

16. The method of claim 15 wherein ring B is selected from the group consisting of phenyl, 4-hydroxyphenyl, 4-ethoxyphenyl and 4-fluorophenyl.

17. The method according to claim 15, wherein the compound is selected from the group consisting of 3-(biphenyl-4-yl)-3-hydroxy-quinuclidine;
3-(4'-fluorobiphenyl-4-yl)-3-hydroxy-quinuclidine;
3-(4'-ethoxybiphenyl-4-yl)-3-hydroxy-quinuclidine; and
3-(4'-hydroxybiphenyl-4-yl)-3-hydroxy-quinuclidine;

or a pharmaceutically acceptable salt thereof.

* * * * *